US011155582B2

(12) United States Patent
Yoshida et al.

(10) Patent No.: US 11,155,582 B2
(45) Date of Patent: Oct. 26, 2021

(54) ANTIVIRAL PEPTIDE AND USE THEREOF

(71) Applicants: Toagosei Co., Ltd., Tokyo (JP); National University Corporation Hokkaido University, Sapporo (JP)

(72) Inventors: Tetsuhiko Yoshida, Tsukuba (JP); Ayato Takada, Sapporo (JP); Nahoko Baileykobayashi, Tsukuba (JP)

(73) Assignees: TOAGOSEI CO., LTD, Tokyo (JP); National University Corporation Hokkaido University, Sapporo (JP)

( * ) Notice: Subject to any disclaimer, the term of this patent is extended or adjusted under 35 U.S.C. 154(b) by 0 days.

(21) Appl. No.: 16/591,706

(22) Filed: Oct. 3, 2019

(65) Prior Publication Data
US 2020/0109177 A1    Apr. 9, 2020

(30) Foreign Application Priority Data
Oct. 9, 2018    (JP) .............................. JP2018-190663

(51) Int. Cl.
| *C07K 14/005* | (2006.01) |
| *C07K 14/47* | (2006.01) |
| *A61K 38/00* | (2006.01) |
| *C12N 7/00* | (2006.01) |
| *A61P 31/14* | (2006.01) |

(52) U.S. Cl.
CPC ............ *C07K 14/005* (2013.01); *A61P 31/14* (2018.01); *C07K 14/47* (2013.01); *C12N 7/00* (2013.01); *A61K 38/00* (2013.01); *C07K 2319/03* (2013.01); *C07K 2319/33* (2013.01); *C12N 2760/20222* (2013.01); *C12N 2760/20233* (2013.01); *C12N 2760/20271* (2013.01)

(58) Field of Classification Search
None
See application file for complete search history.

(56) References Cited

U.S. PATENT DOCUMENTS

2009/0012000 A1    1/2009    Yoshida et al.
2009/0258815 A1   10/2009    Yoshida et al.

FOREIGN PATENT DOCUMENTS

JP    2007-230903    9/2007
JP    2007-230904    9/2007

OTHER PUBLICATIONS

Delcroix et al. (Pharmaceuticals 2010, 3,448-470) (Year: 2010).*
Georgel et al. (Virology 362 (2007) 304-313) (Year: 2007).*
GenBank ADC43008.1 (downloaded on Jan. 27, 2020 from URL:<https://www.ncbi.nlm.nih.gov/protein/ADC43008.1>) (Year: 2020).*

* cited by examiner

*Primary Examiner* — Sergio Coffa
(74) *Attorney, Agent, or Firm* — Occhiuti & Rohlicek LLP

(57) ABSTRACT

An antiviral peptide provided according to the present invention includes (1) an amino acid sequence (TM sequence) constituting a transmembrane region of G protein of vesicular stomatitis virus (VSV) or a modified amino acid sequence formed by conservative substitutions of 1, 2, or 3 amino acid residues in the TM sequence; and (2) an amino acid sequence (CPP sequence) functioning as a cell penetrating peptide (CPP), wherein a total number of amino acid residues is 100 or less.

13 Claims, 8 Drawing Sheets
Specification includes a Sequence Listing.

ANTIVIRAL PEPTIDE AND USE THEREOF

CROSS-REFERENCE TO RELATED APPLICATIONS

Priority is claimed on Japanese Patent Application No. 2018-190663, filed Oct. 9, 2018, the content of which is incorporated herein by reference.

TECHNICAL FIELD

The present invention relates to an artificially synthesized antiviral peptide having antiviral activity against at least one type of virus and use thereof, and specifically, to use of an artificial peptide comprising an amino acid sequence (hereinafter referred to as a "TM sequence") composing a transmembrane (TM) peptide derived from some virus strains of vesicular stomatitis virus (VSV) and a membrane penetrating peptide sequence.

TECHNICAL BACKGROUND

Vesicular stomatitis virus (VSV) belonging to the genus Vesiculovirus of the family Rhabdoviridae as an RNA virus has a high infectivity titer and is important as a pathogenic virus that causes vesicular stomatitis which is one of animal diseases. Currently, there is no vaccine against VSV and no effective treatment methods against infected animals have been established. On the other hand, VSV has been used as a virus vector in various research fields because it has high proliferative and virological properties. In addition, in recent years, recombinant viruses that express proteins of different species of viruses have been produced in the structure of a certain virus using a method of virus reverse genetics, and have been used as tools for analyzing viral protein functions, interactions with host cells, pathogenesis mechanisms, and the like in detail. For example, recombinant viruses having a VSV structure can be used in vaccines and as tools for disease treatment.

At present, there are many viral diseases of which treatments are limited to symptomatic treatments because there are no effective vaccines and antiviral agents. In addition, due to the emergence of drug-resistant viruses, in some cases, existing therapeutic agents cannot be selected and sufficient treatment cannot be performed. Therefore, the development of antiviral agents with different functional mechanisms and chemical characteristics against viral diseases has been actively conducted. As one of approaches thereof, the development of naturally derived or artificially produced antiviral peptides that can prevent or reduce viral infection and proliferation has been conducted. Refer to, for example, Japanese Patent Application Publication No. 2007-230904 and Japanese Patent Application Publication No. 2007-230903.

SUMMARY OF THE INVENTION

An object of the present invention is to design a novel artificial antiviral peptide which is a peptide having a structure different from antiviral peptides described in the above patent documents, and is different from peptides that are present and function as antiviral peptides in nature. In addition, another object of the present invention is to provide an antiviral composition (typically, an antiviral agent or a research reagent as a pharmaceutical composition) obtained when the antiviral peptide designed according to the present invention is produced and the peptide is incorporated as a main component.

The inventors focused on amino acid sequence of glycoproteins (hereinafter referred to as "G protein") encoded by G gene of VSV. Thus, surprisingly, the inventors found that a synthetic peptide in which TM sequences of G proteins and amino acid sequences functioning as conventionally known cell penetrating peptides (hereinafter referred to as "CPP sequence") are combined has excellent antiviral activity against at least one type of virus (typically, activity to inhibit virus proliferation, and activity to inhibit viral infection), and completed the present invention.

That is, the synthetic peptide disclosed here is an antiviral peptide having antiviral activity against at least one type of virus.

The peptide comprises the following (1) and (2) amino acid sequences:

(1) an amino acid sequence composing a transmembrane region (TM sequence) of glycoprotein (G protein) encoded by a G gene of vesicular stomatitis virus (VSV), or a modified amino acid sequence formed by conservative substitutions of 1, 2, or 3 amino acid residues in the TM sequence; and (2) an amino acid sequence (CPP sequence) that functions as a cell penetrating peptide (CPP).

In a preferable aspect, the total number of amino acid residues of the antiviral peptide disclosed herein is 100 or less. In consideration of production costs, ease of synthesis, and handling properties, more preferably, the total number of amino acid residues is 80 or less (for example, 60 or less, and more preferably 50 or less, or 40 or less).

Alternatively, a synthetic peptide in which the number of amino acid residues of the amino acid sequence indicated in the above (1) and the amino acid sequence indicated in the above (2) in combination is 80% or more (more preferably 90% or more, for example, 100%) of the total number of amino acid residues of the antiviral peptide is a particularly suitable aspect among the antiviral peptides disclosed here.

In another suitable aspect of the antiviral peptide disclosed here, the TM sequence in the above (1) is an amino acid sequence represented by any one of SEQ ID NOs: 1 to 3.

In addition, in another suitable aspect of the antiviral peptide disclosed herein, the amino acid sequence functioning as a CPP in the above (2) is a polyarginine (not particularly limited, but typically composed of 5 or more and 9 or less arginine residues) or an amino acid sequence represented by any one of SEQ ID NOs: 4 to 21, or a modified amino acid sequence formed by conservative substitutions of 1, 2, or 3 amino acid residues in the amino acid sequence.

In the antiviral peptide disclosed herein, preferably, the CPP sequence in the above (2) is arranged on the N terminal side or C terminal side of the TM sequence of the above (1) directly or via a linker composed of 1, 2, or 3 amino acid residues.

Another suitable aspect of the antiviral peptide disclosed herein comprises an amino acid sequence of SEQ ID NOs: 22 to 24.

In addition, the present invention provides an antiviral composition inhibiting proliferation of at least one type of virus, the antiviral composition including any of the synthetic peptides (antiviral peptides) disclosed herein and at least one pharmaceutically acceptable carrier.

Such a composition containing the antiviral peptides disclosed here can be used as an antiviral agent or a research material for development of a novel antiviral agent.

In addition, the present invention provides a method of inhibiting proliferation of at least one type of virus, the method including supplying any of the synthetic peptides (antiviral peptides) disclosed herein to subject cells, tissues, or the like (for example, outside a living organism=in vitro or inside a living organism=in vivo) at least once.

In the method in such a configuration, when the antiviral peptide disclosed herein is supplied to a subject, it is possible to prevent or inhibit proliferation of at least one type of virus (for example, VSV).

DESCRIPTION OF THE RELATED EMBODIMENTS

Figure 1:
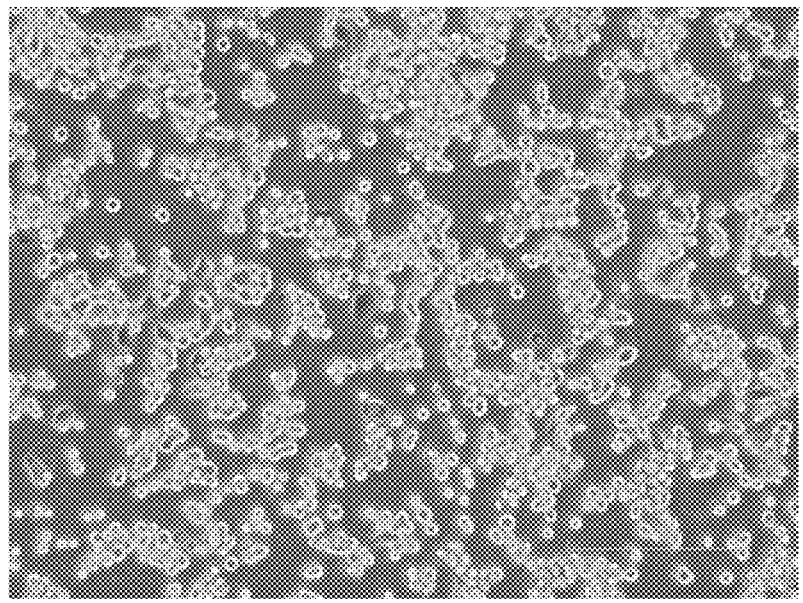
FIG. 1 is photomicrographic image of Vero E6 cells that were cultured for 1 day without addition of antiviral peptides after inoculation of VSV ($10^3$ PFU/well).

Preferable embodiments of the present invention will be described below. Components other than those particularly mentioned in this specification (for example, the primary structure and chain length of synthetic peptides disclosed here) that are necessary for implementation of the present invention (for example, a method of chemically synthesizing peptides, a cell culture technique, and a general method of preparing an antiviral composition including a peptide disclosed here as a component) can be recognized by those skilled in the art as design matters based on the related art in the fields of cell engineering, physiology, medicine, pharmacy, organic chemistry, biochemistry, genetic engineering, protein engineering, molecular biology, genetics, and the like. The present invention can be implemented based on content disclosed in this specification and common general technical knowledge in the field. Here, in the following description, amino acids are represented by one-letter symbols (but, three-letter symbols in the sequence listing).

The entire content of all documents cited in this specification is incorporated herein by reference.

The "artificially synthesized peptide" in this specification refers to a peptide fragment of which a peptide chain alone is not independently and stably present in nature, but it is produced through artificial chemical synthesis or biosynthesis (that is, production based on genetic engineering), and can be stably present in a predetermined system (for example, a composition constituting an antiviral agent). The term "peptide" herein refers to an amino acid polymer having a plurality of peptide bonds, and although the number of amino acid residues contained in the peptide chain is not limited, the peptide has a relatively low molecular weight, typically, a total number of amino acid residues of about 100 or less (preferably 80 or less, and more preferably 50 or less, for example, 40 or less).

In addition, the term "amino acid residue" in this specification includes an N terminal amino acid and a C terminal amino acid of a peptide chain unless otherwise specified.

Here, the left side of the amino acid sequence described in this specification is always the N terminal side, and the right side thereof is the C terminal side.

The "modified amino acid sequence" with respect to a predetermined amino acid sequence in this specification refers to an amino acid sequence formed by substitution, deletion, or addition (insertion) of 1 to more (typically, 9 or less, preferably 5 or less) amino acid residues, for example, 1, 2, or 3 amino acid residues, without impairing functions (for example, antiviral activity and cell membrane penetrating ability) of the predetermined amino acid sequence. For example, a sequence generated by so-called conservative amino acid substitution in which 1, 2, or 3 amino acid residues are conservatively substituted (for example, a sequence in which a basic amino acid residue is substituted by another basic amino acid residue: for example, a lysine residue and an arginine residue are substituted by each other), a sequence in which 1, 2, or 3 amino acid residues are added (inserted) to or deleted from a predetermined amino acid sequence, and the like are typical examples included in the modified amino acid sequence referred to in this specification.

Therefore, specific examples of the antiviral peptide disclosed herein include, in addition to synthetic peptides composed of the same amino acid sequences as amino acid sequences represented by SEQ ID NOs as described below, synthetic peptides composed of modified amino acid sequences in which 1, 2, or 3 amino acid residues are substituted (typically, conservative amino acid substitution), deleted, or added in amino acid sequences represented by the SEQ ID NOs, which are modified amino acid sequences, exhibiting the same antiviral activity as the amino acid sequences represented by the SEQ ID NOs.

The artificially synthesized antiviral peptide disclosed herein is a short chain peptide that does not occur in nature, and is a peptide comprising the two amino acid sequences, that is,
(1) TM sequence of G protein, or a modified amino acid sequence formed by conservative substitution of 1, 2, or 3 amino acid residues in the TM sequence; and
(2) an amino acid sequence functioning as a CPP (CPP sequence).

G protein is a transmembrane type I glycoprotein and has been used as a glycoprotein constituting the envelope in a "retroviral vector" in recent years. However, it has not been found that the TM region of G protein has antiviral activity, and the fact that an artificially synthesized antiviral peptide is obtained by synthesizing an amino acid sequence of such a TM region and adding a CPP to the sequence was completely unexpected at the time of filing of this application. In addition, as shown in SEQ ID NOs: 1 to 3, the TM sequence differs depending on the serotype of VSV, but the fact that synthetic peptides having any TM sequence have excellent antiviral activity was also completely unexpected at the time of filing of this application.

Here, amino acid sequence information of each G protein can be easily obtained by accessing knowledge bases (databases) in various public international organizations. For example, anyone can easily obtain all amino acid sequence information of such glycoproteins and amino acid sequence information of TM regions registered in the database (UniProtKB) in Universal Protein Resource (UniProt).

Although not particularly limited, SEQ ID NOs: 1 to 3 are preferred examples of the TM sequence of G protein. Specifically, the sequence numbers are as follows.

SEQ ID NO: 1 is a TM sequence composed of total 19 amino acid residues contained in G protein of one isolated Vesicular stomatitis Piry virus (VSV) (UniProtKB-Q85213).

SEQ ID NO: 2 is a TM sequence composed of total 21 amino acid residues contained in G protein of one isolated Vesicular stomatitis Indiana virus (VSV) (UniProtKB-P05322).

SEQ ID NO: 3 is a TM sequence composed of total 21 amino acid residues contained in the G protein of one isolated Vesicular stomatitis New Jersey virus (VSV) (UniProtKB-P04882).

Regarding an amino acid sequence functioning as a CPP that is used to construct an antiviral peptide disclosed herein, conventionally known various CPPs can be used. For example, a so-called polyarginine (Rn) composed of 3 or more, preferably 5 or more and 11 or less, and preferably 9 or less arginine residues, is suitable as a CPP used here. In addition, various known CPPs can be used.

Although not particularly limited, SEQ ID NOs: 4 to 21 are preferred examples of a CPP. Specifically, the sequence numbers are as follows.

The amino acid sequence of SEQ ID NO: 4 corresponds to Nucleolar localization signal (NoLS) composed of total 14 amino acid residues derived from FGF2 (basic fibroblast growth factor).

The amino acid sequence of SEQ ID NO: 5 corresponds to NoLS composed of total 19 amino acid residues derived from one nucleolus protein (ApLLP).

The amino acid sequence of SEQ ID NO: 6 corresponds to NoLS composed of total 16 amino acid residues derived from the protein (γ(1) 34.5) of HSV-1 (herpes simplex virus type 1).

The amino acid sequence of SEQ ID NO: 7 corresponds to NoLS composed of total 19 amino acid residues derived from the p40 protein of HIC (human I-mfa domain-containing protein).

The amino acid sequence of SEQ ID NO: 8 corresponds to NoLS composed of total 16 amino acid residues derived from the MEQ protein of MDV (Marek's disease virus).

The amino acid sequence of SEQ ID NO: 9 corresponds to NoLS composed of total 17 amino acid residues derived from Survivin-deltaEx3 which is a protein that inhibits apoptosis.

The amino acid sequence of SEQ ID NO: 10 corresponds to NoLS composed of total 7 amino acid residues derived from Angiogenin which is a vascular growth factor.

The amino acid sequence of SEQ ID NO: 11 corresponds to NoLS composed of total 8 amino acid residues derived from MDM2 which is a nuclear phosphoprotein and forms a complex with the p53 tumor suppression protein.

The amino acid sequence of SEQ ID NO: 12 corresponds to NoLS composed of total 9 amino acid residues derived from GGNNVα which is a betanodaviral protein.

The amino acid sequence of SEQ ID NO: 13 corresponds to NoLS composed of total 7 amino acid residues derived from NF-κB-inducible kinase (NIK).

The amino acid sequence of SEQ ID NO: 14 corresponds to NoLS composed of total 15 amino acid residues derived from the Nuclear VCP-like protein.

The amino acid sequence of SEQ ID NO: 15 corresponds to NoLS composed of total 18 amino acid residues derived from p120 which is a nucleolus protein.

The amino acid sequence of SEQ ID NO: 16 corresponds to NoLS composed of total 14 amino acid residues derived from the ORF57 protein of HVS (herpes virus saimiri).

The amino acid sequence of SEQ ID NO: 17 corresponds to NoLS composed of total 13 amino acid residues from the 491st amino acid residue of LIM Kinase 2 present in human endothelial cells, which is one of protein kinases related to intracellular information transfer, to the 503rd amino acid residue.

The amino acid sequence of SEQ ID NO: 18 corresponds to NoLS composed of total 8 amino acid residues contained in the N protein (nucleocapsid protein) of IBV (avian infectious bronchitis virus).

The amino acid sequence of SEQ ID NO: 19 corresponds to a membrane penetrating motif composed of total 9 amino acid sequences derived from a protein transduction domain contained in TAT of HIV (Human Immunodeficiency Virus).

The amino acid sequence of SEQ ID NO: 20 corresponds to a membrane penetrating motif composed of total 11 amino acid sequences of a protein transduction domain (PTD4) obtained by modifying the above TAT.

The amino acid sequence of SEQ ID NO: 21 corresponds to a membrane penetrating motif composed of total 18 amino acid sequences derived from ANT of Antennapedia which is a variant of Drosophila.

Among these, particularly, amino acid sequences related to NoLS and TAT (or modified amino acid sequences thereof) are preferable. For example, the CPP sequences related to NoLS represented by SEQ ID NO: 17 and SEQ ID NO: 18 or the CPP sequences related to TAT and ANT represented by SEQ ID NOs: 19 to 21 can be suitably used to construct the antiviral peptide disclosed here.

A peptide chain (amino acid sequence) of the antiviral peptide disclosed here may comprise the amino acid sequence indicated in the (1) (hereinafter collectively referred to as "(1) antiviral TM sequence") and the amino acid sequence indicated in the (2) (hereinafter collectively referred to as "(2) CPP sequence"), and either the (1) antiviral TM sequence or the (2) CPP sequence may be relatively arranged on the N terminal side (C terminal side).

Preferably, the (1) antiviral TM sequence and the (2) CPP sequence are directly arranged. In a specific aspect, preferably, there are no amino acid residues that are not included in both sequence parts between the (1) antiviral TM sequence and the (2) CPP sequence. Alternatively, in another aspect, preferably, the above two sequences are arranged via a linker composed of 10 amino acid residues or less (more preferably, 5 or less, for example, 1, 2, or 3 amino acid residues).

In addition, as long as the antiviral activity with which proliferation of at least one type of virus can be inhibited is not impaired, the antiviral peptide may contain a sequence (amino acid residue) part other than the amino acid sequence constituting the (1) antiviral TM sequence and the (2) CPP sequence.

In the antiviral peptide disclosed here, a total number of amino acid residues composing the peptide chain is suitably 100 or less, preferably 80 or less, and preferably 70 or less or 60 or less (for example, a peptide chain of about 25±2 to 50±2). Such a peptide with a short chain length is easily chemically synthesized and an antiviral peptide can be easily provided. Although not particularly limited, a linear or helical form is preferable because it is less likely to become an immunogen (antigen). A peptide in such a form is less likely to constitute an epitope.

A proportion of the number of amino acid residues of the (1) antiviral TM sequence and the (2) CPP sequence in combination with respect to the total number of amino acid residues of the synthesized peptide is not particularly limited as long as the antiviral activity is not impaired, but the proportion is desirably about 80% or more, or preferably 90% or more. Here, it is preferable that all amino acid residues be L-type amino acids. However, some or all of amino acid residues may be replaced with D-type amino acids as long as the antiviral activity is not impaired.

Preferably, in the antiviral peptide disclosed here, at least one amino acid residue is preferably amidated. When a carboxyl group of an amino acid residue (typically, a C terminal amino acid residue of the peptide chain) is amidated, it is possible to improve structural stability (for example, protease resistance) of the synthetic peptide.

In one aspect, when a CPP sequence constitutes a C terminal part of the antiviral peptide disclosed here, the C terminal amino acid residue of the antiviral TM sequence is amidated. On the other hand, in another suitable aspect, when a CPP sequence constitutes a C terminal part of the antiviral peptide, the C terminal amino acid residue of the CPP sequence is amidated to stabilize the antiviral peptide.

The antiviral peptide disclosed here can be easily produced according to a general chemical synthesis method. For example, any of conventionally known solid phase synthesis methods and liquid phase synthesis methods may be used. A solid phase synthesis method in which Boc (t-butyloxycarbonyl) or Fmoc (9-fluorenylmethoxycarbonyl) is applied as a protecting group for an amino group is suitable.

Regarding the antiviral peptide disclosed here, a peptide chain having a desired amino acid sequence and a modified (C terminal amidation, etc.) part can be synthesized according to a solid phase synthesis method using a commercially available peptide synthesizer.

Alternatively, an antiviral peptide may be biosynthesized based on a genetic engineering technique. That is, a polynucleotide (typically, DNA) of a nucleotide sequence (including an ATG start codon) that encodes an amino acid sequence of a desired antiviral peptide is synthesized. Then, a recombinant vector having a gene construct for expression composed of the synthesized polynucleotide (DNA) and various regulating elements (including promoters, ribosome binding sites, terminators, enhancers, and various cis elements that control an expression level) for expressing the amino acid sequence in host cells is constructed according to host cells.

According to a general technique, the recombinant vector is introduced into predetermined host cells (for example, yeast, insect cells, and plant cells), and the host cells or tissues or subjects containing the cells are cultured using predetermined conditions. Accordingly, desired peptides can be expressed and produced in cells. Then, peptides are isolated from the host cells (in a culture medium if secreted), and as necessary, refolding, purification, and the like are performed, and thereby a desired antiviral peptide can be obtained.

Here, regarding a method of constructing a recombinant vector, a method of introducing host cells into a constructed recombinant vector, and the like, methods conventionally used in the field may be directly used, and such methods themselves do not particularly characterize the present invention, and thus detailed descriptions thereof will be omitted.

Alternatively, a template DNA (that is, a synthetic gene fragment including a nucleotide sequence that encodes an amino acid sequence of an antiviral peptide) for a cell-free protein synthesis system is constructed, various compounds (ATP, RNA polymerase, amino acids, etc.) necessary for peptide synthesis are used, and thus a desired polypeptide can be synthesized in vitro using a so-called cell-free protein synthesis system. Regarding the cell-free protein synthesis system, refer to, for example, the paper written by Shimizu et al. (Shimizu et al., Nature Biotechnology, 19, 751-755 (2001)), and the paper written by Madin et al. (Madin et al., Proc. Natl. Acad. Sci. USA, 97(2), 559-564 (2000)). Based on the techniques described in these papers, many companies had already commissioned polypeptides at the time of filing this application, and cell-free protein synthesis kits (for example, commercially available from CellFree Sciences Co., Ltd. Japan) are commercially available.

A single-stranded or double-stranded polynucleotide including a nucleotide sequence that encodes the antiviral peptide disclosed here and/or a nucleotide sequence complementary to the sequence can be easily produced (synthesized) by conventionally known methods. That is, when codons corresponding to amino acid residues constituting a designed amino acid sequence are selected, a nucleotide sequence corresponding to the amino acid sequence of the antiviral peptide is easily determined and provided. Then, once the nucleotide sequence is determined, a (single-stranded) polynucleotide corresponding to a desired nucleotide sequence can be easily obtained using a DNA synthesizer or the like. In addition, desired double-stranded DNA can be obtained using the obtained single-stranded DNA as a template according to various enzymatic synthesis techniques (typically, PCR). In addition, the polynucleotide may be in the form of DNA or in the form of RNA (mRNA, etc.). Double-stranded or single-stranded DNA may be provided. When single-stranded DNA is provided, it may be a coding strand (sense strand) or a non-coding strand (antisense strand) of a sequence complementary thereto.

The polynucleotide obtained in this manner can be used as a material for constructing a recombinant gene (expression cassette) for antiviral peptide production in various host cells or a cell-free protein synthesis system as described above.

The antiviral peptide disclosed here has high antiviral activity against at least one type of virus (for example, VSV). For example, it can be used for the purpose of treatment and prevention of infectious diseases due to this type of virus, for example, cleaning of the mouth (gargling), cleaning of the eyes, or cleaning of devices.

Here, the antiviral peptide contained in the antiviral composition (antiviral agent) may be in a salt form as long as the antiviral activity is not impaired. For example, an acid addition salt of the peptide that can be obtained by an addition reaction of an inorganic acid or organic acid that is generally used according to a general method can be used. Alternatively, it may be in another salt form (for example, a metal salt) as long as it has antiviral activity. Therefore, the "peptide" described in this specification and the claims includes such salt forms.

The antiviral composition disclosed herein can contain various pharmaceutically (pharmacologically) acceptable carriers according to the usage form as long as the antiviral activity of the antiviral peptide as an effective component is not impaired. For example, carriers that are generally used in the peptide-based drug can be applied as a diluent, an excipient, and the like.

The carrier may appropriately vary depending on applications and forms of the antiviral composition disclosed here, but typically, water, a physiological buffer solution, and various organic solvents may be exemplified. The carrier may be a non-drying oil such as an aqueous solution containing an alcohol (such as ethanol) with an appropriate concentration, glycerol, and olive oil. Alternatively, it may be a liposome. In addition, examples of a secondary component that can be contained in the antiviral composition include various fillers, extending agents, binders, moisturizers, surfactants, pigments, and perfumes.

Examples of typical forms of the antiviral composition (antiviral agent) include solutions, suspending agents, emulsions, aerosols, foam agents, granules, powders, tablets, capsules, ointments, and aqueous gels. In addition, for use in injection or the like, lyophilizates and granules for preparing a drug solution by performing dissolving in a saline or a suitable buffer solution (for example, PBS) immediately before use can be provided.

Here, a process itself of preparing various forms of compositions (drugs) including the antiviral peptide (main component) and various carriers (secondary component) as materials may be performed according to a conventionally known method, and such a production method itself does not characterize the present invention, and thus detailed description thereof will be omitted. Examples of detailed sources of information on prescription include Comprehensive Medicinal Chemistry, edited by Corwin Hansch, Pergamon Press (1990). The entire content in this book is incorporated by reference.

The antiviral composition disclosed herein (antiviral agent) can be used according to a method and in a dose depending its form and purpose.

The antiviral peptide disclosed here can maintain antiviral activity also in a system in which cations with a relatively high concentration, salts (for example, sodium chloride), or organic substances such as serum are present. Therefore, the antiviral composition disclosed here is suitable for use in a system (form) in which cations, salts, serum, and the like are present. For example, the antiviral composition provided according to the present invention can be administered to patients, as a solution, through intravenous, intramuscular, subcutaneous, intradermal or intraperitoneal injection or enema.

Alternatively, a solid form such as a tablet can be administered orally. In addition, when used for cleaning the surface of sanitary ware, a solution containing a relatively large amount (for example, 1 to 100 mg/mL) of antiviral peptide may be directly sprayed to the surface of an object, or the surface of an object may be wiped with cloth or paper wet with the solution. These are only examples, and the same forms and use methods as with pesticides including conventional peptide-based antibiotics or peptides as constituent components, quasi-drugs, and the like can be used.

In addition, a polynucleotide that encodes an antiviral peptide can be used as a material that is used for so-called gene therapy. For example, a gene (typically, a DNA segment or an RNA segment) that encodes an antiviral peptide is incorporated into a suitable vector, and introduced into a desired part, and thus the antiviral peptide according to the present invention can be expressed in a living body (cells) constantly. Therefore, a polynucleotide (a DNA segment, an RNA segment, etc.) that encodes the antiviral peptide of the present invention is beneficial as a drug for preventing or treating viral infection.

In the field of genetic engineering in recent years, regarding a virus vector for introducing a target gene into cells, tissues, or organs, a recombinant VSV has been used. In addition, in order to analyze functions of viral proteins of other virus species (for example, retrovirus), a pseudo type virus in which G protein of VSV is incorporated may be used. For example, as shown in examples to be described below, when the antiviral peptide disclosed here with an appropriate concentration is contained in a culture solution, it is possible to prevent undesired viral infection in organs, tissues, cells and the like during culture, or inhibit virus proliferation in the host.

In addition, in the development of vaccines and antiviral therapeutic agents, detailed information on pathogenic viruses is necessary. For example, as shown in examples to be described below, the antiviral peptide disclosed here can be applied as a research tool for analyzing an infection and proliferation mechanism of VSV.

In addition, for breeding environment management and quality management of domestic animals, it is essential to prevent and treat (for example, vaccines and antiviral therapeutic agents) diseases of domestic animals, and it is necessary obtain information about the exact pathogens causing diseases. Since the antiviral peptide disclosed here itself can be a promising seed for an anti-VSV agent, it can prevent viral infection of domestic animals, and prevent spread of infection among domestic animals, and furthermore, it can be expected to establish infection prevention and treatment methods for domestic animal workers and veterinarians who are in close contact with domestic animals.

While several examples of the present invention will be described below, these examples are not intended to limit the present invention.

TABLE 1

Table 1

| Sample No. | Amino acid sequence | Total number of amino acid residues | SEQ ID NO |
|---|---|---|---|
| 1 | MAIVGIVLLIVVTFLAIKTKKRTLRKNDRKKR-CONH$_2$ | 32 | 22 |
| 2 | FFFIIGLIIGLFLVLRVGIHLKKRTLRKNDRKKR-CONH$_2$ | 34 | 23 |
| 3 | VLAVIIGFVILMFLIKLIGVLKKRTLRKNDRKKR-CONH$_2$ | 34 | 24 |

Test Example 1: Synthesis of Peptide and Preparation of Peptide-Containing Culture Medium Total 3 peptides indicated in Table 1 were produced using a commercially available peptide synthesizer. Specifically, details are as follows.

Sample 1, shown in SEQ ID NO: 22, was a synthetic peptide using, as the (1) antiviral TM sequence, an amino acid sequence (TM sequence of G protein of VSV Piry strain) represented by SEQ ID NO: 1, and including, as the (2) CPP sequence, an amino acid sequence (NoLS of LIM kinase 2) of SEQ ID NO: 17, on the C terminal side.

Sample 2, shown in SEQ ID NO: 23, was a synthetic peptide using, as the (1) antiviral TM sequence, an amino acid sequence (TM sequence of G protein of VSV Indiana strain) represented by SEQ ID NO: 2, and including, as the (2) CPP sequence, an amino acid sequence (NoLS of LIM kinase 2) of SEQ ID NO: 17, on the C terminal side.

Sample 3, shown in SEQ ID NO: 24, was a synthetic peptide using, as the (1) antiviral TM sequence, an amino acid sequence (TM sequence of G protein of VSV New Jersey strain) represented by SEQ ID NO: 3, and including, as the (2) CPP sequence, an amino acid sequence (NoLS of LIM kinase 2) of SEQ ID NO: 17, on the C terminal side.

All the peptides of Samples 1 to 3 were synthesized by performing a solid phase synthesis method (Fmoc method) manually using a commercially available peptide synthesizer. Here, since a manner of use of the peptide synthesizer itself does not characterize the present invention, detailed description thereof will be omitted. In all synthetic peptides subjected to the test, a carboxyl group (—COOH) of the C terminal amino acid was amidated (—CONH$_2$).

The synthesized peptides of the samples were dissolved in DMSO (dimethyl sulfoxide), and stock solutions (with a concentration of 2.5 mM) containing the sample peptides were prepared.

Test Example 2: Test of Evaluating Antiviral Activity of Synthetic Peptides

Details of cells and viruses used in this test are as follows.

For culture of African green monkey kidney epithelium Vero E6 cells, Dulbecco's Modified Eagle Medium (DMEM) supplemented with L-glutamine, 100 U/mL of penicillin, 0.1 mg/mL of streptomycin, and 10% FCS was used.

The target virus was VSV, and its virus titer (infectivity titer) was measured based on a known general plaque assay method.

Details of Test Example 2 are as follows.

First, VSV prepared in advance was appropriately diluted to prepare a virus suspension with an infectivity titer of $10^2$ PFU/mL or $10^3$ PFU/mL. DMEM supplemented with 2% FCS was used for dilution of the virus solution.

Vero E6 cells cultured in a commercially available 6-well plate in advance were washed with 1 mL of PBS per well and then inoculated with 1 mL of virus with the above infectivity titer for each well. That is, an amount of inoculated virus per well was $10^2$ PFU or $10^3$ PFU. The virus was inoculated and incubated at 37° C. for about 1 hour, and the inoculated virus suspension was then removed from each well, and each well was washed once with PBS and DMEM.

Then, 2 mL of DMEM supplemented with 2% FCS containing any of the above sample peptides prepared was supplied to each well, and cultured at 37° C. The concentration of the sample peptide was 10 μM, and regarding an experiment control, DMEM supplemented with 2% FCS in which DMSO was added in the same amount as a solvent contained in a sample peptide preparation solution was used.

1 day after the culture was started, a culture supernatant was collected, and an infectivity titer of the virus in the culture supernatant was calculated as an amount of virus according to a known general TCID 50 method using Vero E6 cells not infected with virus. The results are shown in Tables 2 and 3 and FIGS. 1 and 2. In the tables, the amount is shown as a numerical value of $Log_{10}$ TCID 50/mL. A lower value indicates a lower amount of infectious virus particles in the culture supernatant.

TABLE 2

Table 2: Amount of virus inoculated 100 PFU/well

| Test samples | Amount of virus in culture supernatant ($Log_{10}$ TCID 50/mL) |
|---|---|
| Sample 1 | 4.4 |
| Sample 2 | 4.7 |

TABLE 2-continued

Table 2: Amount of virus inoculated 100 PFU/well

| Test samples | Amount of virus in culture supernatant ($Log_{10}$ TCID 50/mL) |
|---|---|
| Sample 3 | 4.7 |
| Control | 8.3 |

TABLE 3

Table 3: Amount of virus inoculated 1000 PFU/well

| Test samples | Amount of virus in culture supernatant ($Log_{10}$ TCID 50/mL) |
|---|---|
| Sample 1 | 5 |
| Sample 2 | 3.5 |
| Sample 3 | 4.5 |
| Control | 8.67 |

Tables 2 and 3 show amounts of virus in the culture supernatant after $10^2$ PFU/well and $10^3$ PFU/well of VSV were inoculated and cultured for 1 day. As can be clearly understood from a logarithmic value of the virus infectivity titer shown in Table 2, in all the sample peptides 1 to 3, a significant proliferation inhibition effect (antiviral) was confirmed with respect to VSV in the inoculation amount of the above two points.

Figure 2:
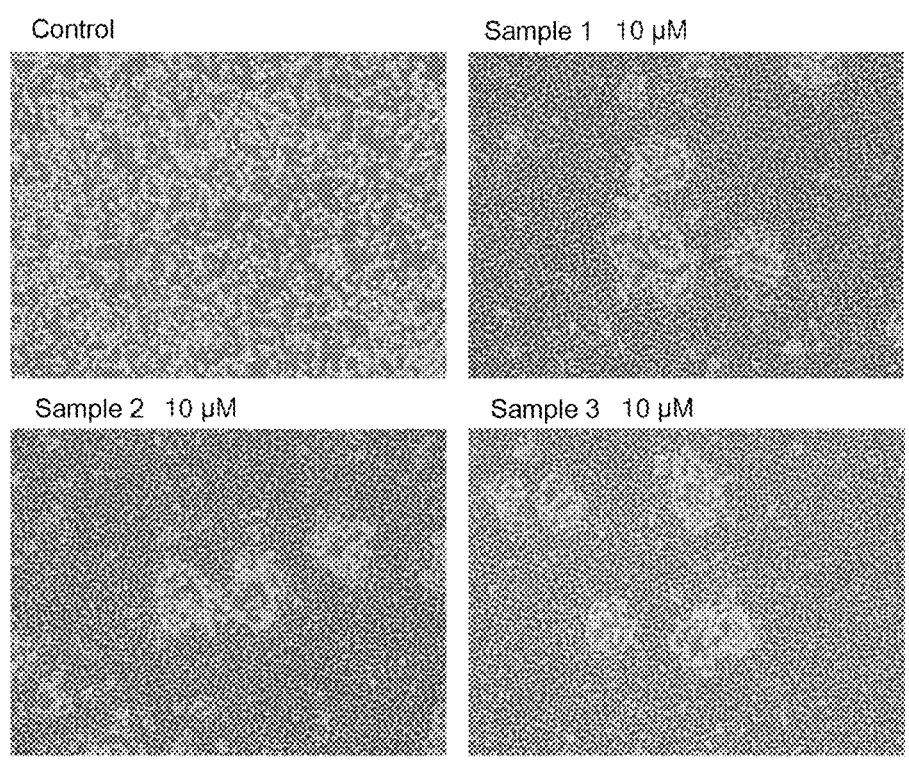
FIG. 2 shows photomicrographic images of Vero E6 cells that were cultured for 1 day when 10 μM of any of three antiviral peptides (Sample 1, Sample 2, and Sample 3) was added or without any addition after inoculation of VSV ($10^3$ PFU/well). Specifically, the upper left part in FIG. 2 shows an observation image of cells that were cultured without addition of antiviral peptides. The upper right part shows an observation image of cells that were cultured in the presence of Sample 1. The lower left part shows an observation image of cells that were cultured in the presence of Sample 2. The lower right part shows an observation image of cells that were cultured in the presence of Sample 3.

FIGS. 1 and 2 show microscopic images of cells obtained 1 day after $10^3$ PFU/well of VSV was inoculated and cultured. As shown here, in the control that was not treated with the sample peptide (FIGS. 1 and 2), cells in the observation field were almost dead cells. On the other hand, in the culture in the presence of the sample peptide, dropout of some cells was observed, but monolayer (living cells) of Vero E6 cells were observed in a wide range of the observation field (FIG. 2).

Test Example 3: Test of Evaluating Time Course Antiviral Activity of Synthetic Peptides Test Example 3 was performed under the same conditions as in Test Example 2 except that a concentration of the sample peptide was 50 μM, and the culture supernatant was collected on the 1st, 2nd, and 3rd days. The results are shown in FIGS. 3 to 8. Here, in the 50 μM sample peptide, even after culture for 3 days, no cytotoxicity against VSV non-infected Vero E6 cells was observed.

Figure 3:
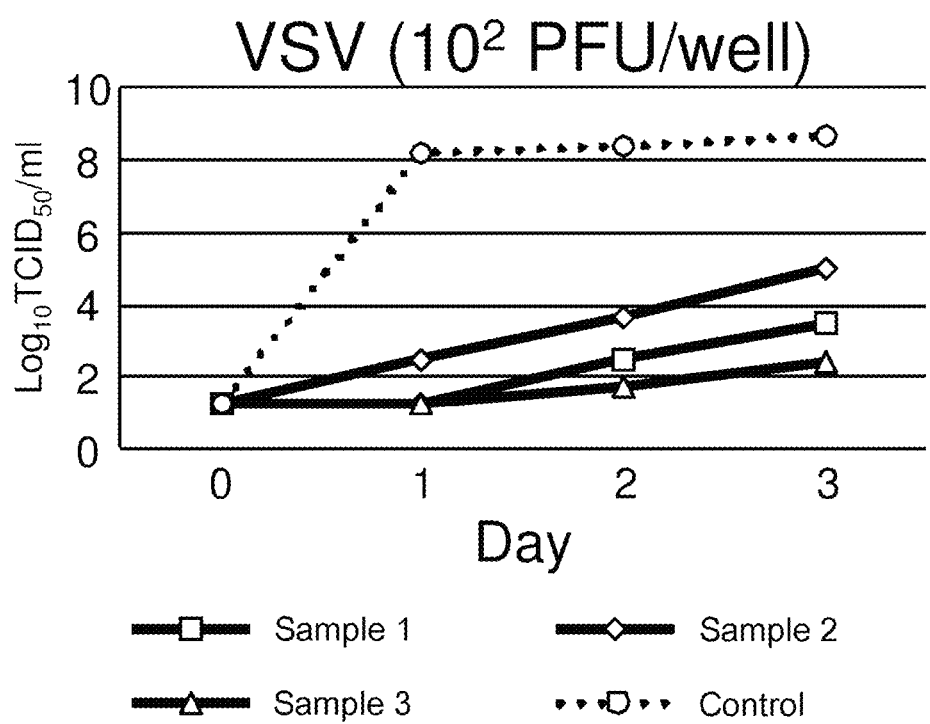
FIG. 3 is a graph showing change in an amount of virus ($Log_{10}$ TCID 50/ml) in a culture supernatant of Vero E6 cells over time that were cultured for 1, 2, and 3 days when 50 μM of any of the three antiviral peptides was added or without any addition after inoculation of VSV ($10^2$ PFU/well).
Figure 4:
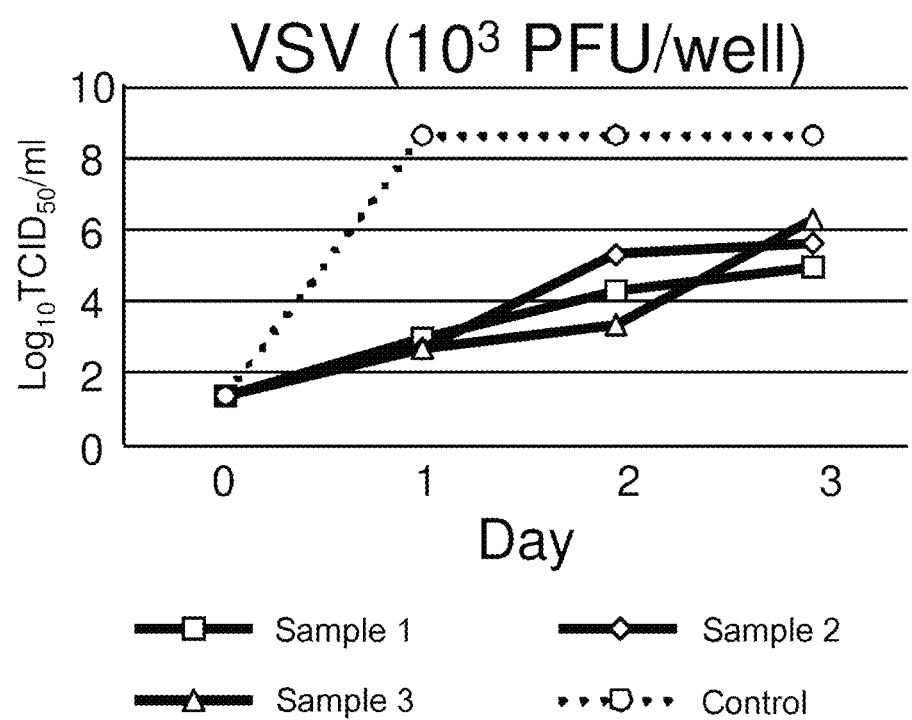
FIG. 4 is a graph showing change in an amount of virus ($Log_{10}$ TCID 50/ml) in a culture supernatant of Vero E6 cells over time that were cultured for 1, 2, and 3 days when 50 μM of any of the three antiviral peptides was added or without any addition after inoculation of VSV ($10^3$ PFU/well).

FIGS. 3 and 4 are graphs showing change in an amount of virus in the culture supernatant over time when $10^2$ PFU/well or $10^3$ PFU/well of VSV was inoculated. As shown in both graphs, sample peptides 1 to 3 had a significantly weak virus proliferation ability for 3 days after virus was inoculated and cultured compared to the control.

Figure 5:
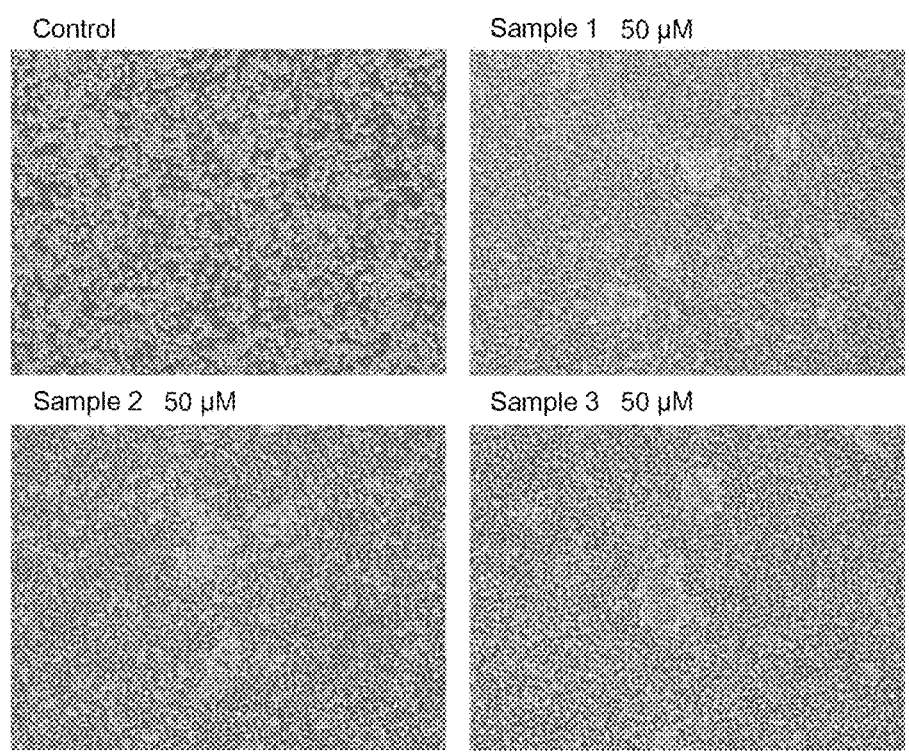
FIG. 5 shows photomicrographic images of Vero E6 cells that were cultured for 1 day when 50 μM of any of the three antiviral peptides was added or without any addition after inoculation of VSV ($10^3$ PFU/well). Specifically, the upper left part in FIG. 5 shows an observation image of cells that were cultured without addition of antiviral peptides. The upper right part shows an observation image of cells that were cultured in the presence of Sample 1. The lower left part shows an observation image of cells that were cultured in the presence of Sample 2. The lower right part shows an observation image of cells that were cultured in the presence of Sample 3.
Figure 6:
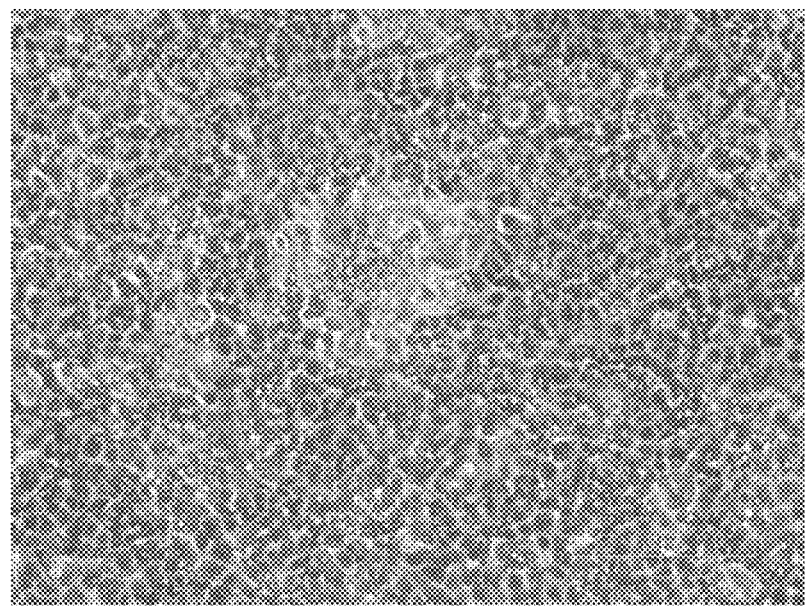
FIG. 6 is a photomicrographic image of Vero E6 cells that were cultured for 1 day when 50 μM of Sample 3 was added after inoculation of VSV ($10^3$ PFU/well).

FIG. 5 shows microscopic images of cells obtained 1 day after $10^3$ PFU/well of VSV was inoculated and cultured. Almost all control cells were dead, but a monolayer of cells treated with the sample peptide was maintained in a wide range. In addition, in cells treated with the sample peptide, while a certain degree of a cytopathic effect (CPE) due to viral infection was observed, no dropout of cells was observed at that time. FIG. 6 shows an enlarged observation image of the CPE part of cells treated with the sample peptide 3. A denatured cell mass due to VSV infection was observed at the center of the image, but cells at the periphery thereof were in a normal form, and 90% or more of the observation field was occupied by a monolayer of living cells.

Figure 7:
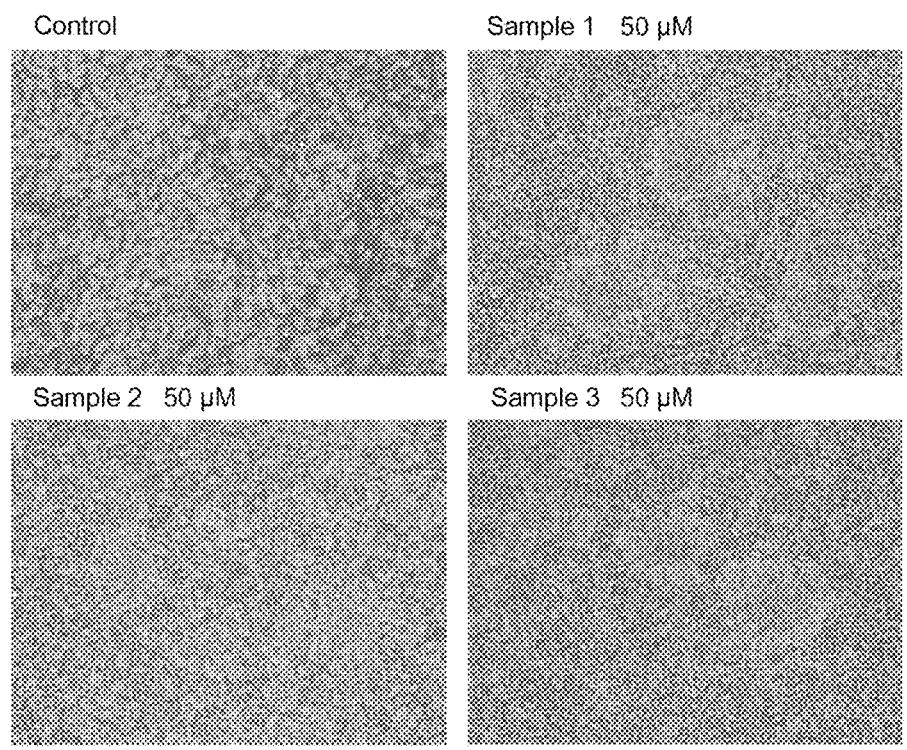
FIG. 7 is a photomicrographic image of Vero E6 cells that were cultured for 2 days when 50 μM of any of the three antiviral peptides was added or without any addition after inoculation of VSV ($10^3$ PFU/well). Specifically, the upper left part in FIG. 7 shows an observation image of cells that were cultured without addition of antiviral peptides. The upper right part shows an observation image of cells that were cultured in the presence of Sample 1. The lower left part shows an observation image of cells that were cultured in the presence of Sample 2. The lower right part shows an observation image of cells that were cultured in the presence of Sample 3.
Figure 8:
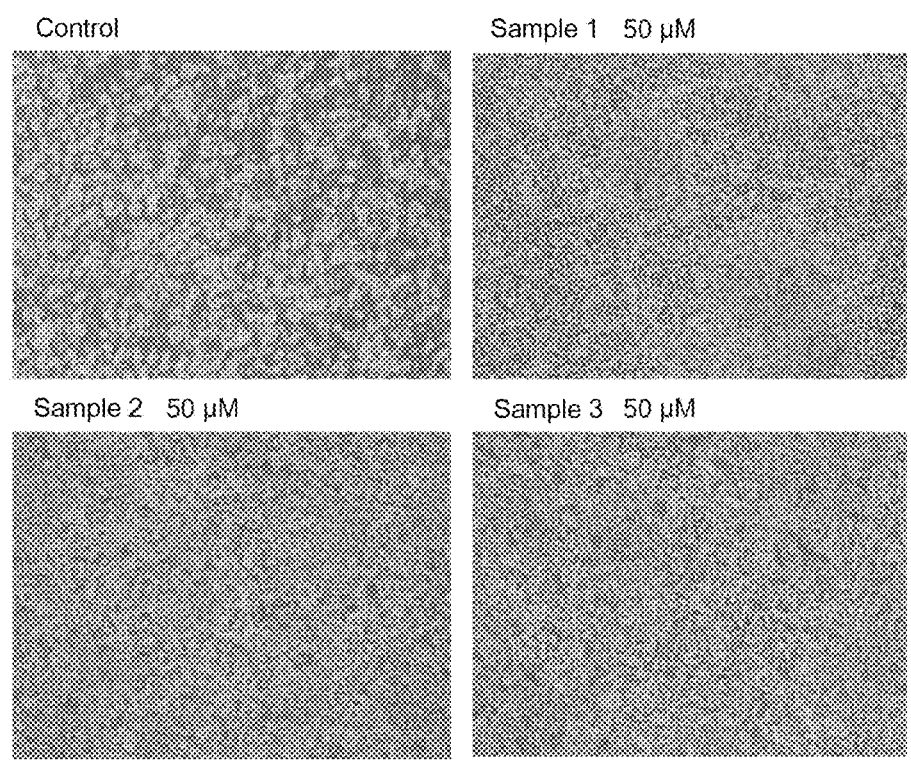
FIG. 8 shows photomicrographic images of Vero E6 cells that were cultured for 3 days when 50 μM of any of the three antiviral peptides was added or without any addition after inoculation of VSV ($10^3$ PFU/well). Specifically, the upper left part in FIG. 8 shows an observation image of cells that were cultured without addition of antiviral peptides. The upper right part shows an observation image of cells that were cultured in the presence of Sample 1. The lower left part shows an observation image of cells that were cultured in the presence of Sample 2. The lower right part shows an observation image of cells that were cultured in the presence of Sample 3.

FIGS. 7 and 8 shows microscopic images obtained 2 and 3 days after $10^3$ PFU/well of VSV was inoculated and cultured. In the culture in the presence of the sample peptide, a monolayer of living cells was observed in a wide range of the observation field also at that time.

While specific examples of the present invention have been described above in detail, these are only examples, and do not limit the scope of the invention. The technologies described in the claims of the invention include various modifications and alternations of the above exemplified specific examples.

For example, while amino acid sequences represented by SEQ ID NOs: 1 to 3 have been used as the (1) antiviral TM sequence in the present example, modified sequences thereof may be used. In addition, while an amino acid sequence represented by SEQ ID NO: 17 has been used as the (2) CPP sequence in the present example, other known (2) CPP sequences (for example, amino acid sequences represented by SEQ ID NOs: 4 to 21), or modified sequences thereof may be used.

As described above, it is possible to inhibit proliferation of viruses (or prevent spread of viral infection) according to the antiviral peptide disclosed here. Therefore, it is possible to provide an antiviral composition (antiviral agent) having an effect of inhibiting proliferation of at least one type of virus using the antiviral peptide provided according to the present invention.

The invention claimed is:

1. A synthetic peptide inhibiting proliferation of at least one type of virus, the synthetic peptide comprising,
    (1) an amino acid sequence represented by any one of SEQ ID NOs: 1 to 3; and
    (2) a cell penetrating peptide (CPP) sequence being a polyarginine or an amino acid sequence represented by any one of SEQ ID NOs: 4 to 21,
    wherein the number of amino acid residues of the above (1) amino acid sequence and (2) CPP sequence in combination is 80% or more of the total number of amino acid residues of the synthetic peptide.

2. The synthetic peptide according to claim 1, wherein said synthetic peptide consists of the above (1) amino acid sequence and (2) CPP sequence.

3. The synthetic peptide according to claim 1, wherein the CPP sequence is arranged on the N terminal side or C terminal side of the amino acid sequence represented by any one of SEQ ID NOs: 1 to 3 directly or via a linker composed of 1, 2, or 3 amino acid residues.

4. The synthetic peptide according to claim 1, comprising an amino acid sequence represented by any one of SEQ ID NOs: 22 to 24.

5. An antiviral composition inhibiting proliferation of at least one type of virus, the antiviral composition comprising:
    a synthetic peptide; and
    at least one pharmaceutically acceptable carrier,
    wherein the synthetic peptide comprises
    (1) an amino acid sequence represented by any one of SEQ ID NOs: 1 to 3; and
    (2) a cell penetrating peptide (CPP) sequence being a polyarginine or an amino acid sequence represented by any one of SEQ ID NOs: 4 to 21, and the number of amino acid residues of the above (1) amino acid sequence and (2) CPP sequence in combination is 80% or more of the total number of amino acid residues of the synthetic peptide.

6. The antiviral composition according to claim 5, wherein said synthetic peptide consists of the above (1) amino acid sequence and (2) CPP sequence.

7. The antiviral composition according to claim 5, wherein the CPP sequence is arranged on the N terminal side or C terminal side of the amino acid sequence represented by any one of SEQ ID NOs: 1 to 3 directly or via a linker composed of 1, 2, or 3 amino acid residues.

8. The antiviral composition according to claim 5, wherein the synthetic peptide comprises an amino acid sequence represented by any one of SEQ ID NOs: 22 to 24.

9. A method of inhibiting proliferation of at least one type of virus, the method comprising:
    supplying a synthetic peptide to a subject at least once, wherein the synthetic peptide comprises:
    (1) an amino acid sequence represented by any one of SEQ ID NOs: 1 to 3; and
    (2) a cell penetrating peptide (CPP) sequence being a polyarginine or an amino acid sequence represented by any one of SEQ ID NOs: 4 to 21,
    wherein the number of amino acid residues of the above (1) amino acid sequence and (2) CPP sequence in combination is 80% or more of the total number of amino acid residues of the synthetic peptide.

10. The method according to claim 9, wherein said synthetic peptide consists of the above (1) amino acid sequence and (2) CPP sequence.

11. The method according to claim 9, wherein the CPP sequence is arranged on the N terminal side or C terminal side of the amino acid sequence represented by any one of SEQ ID NOs: 1 to 3 directly or via a linker composed of 1, 2, or 3 amino acid residues.

12. The method according to claim 9, wherein the synthetic peptide comprises an amino acid sequence represented by any one of SEQ ID NOs: 22 to 24.

13. The method according to claim 9, wherein the virus is vesicular stomatitis virus (VSV).

* * * * *

SEQUENCE LISTING

<160> NUMBER OF SEQ ID NOS: 24

<210> SEQ ID NO 1
<211> LENGTH: 19
<212> TYPE: PRT
<213> ORGANISM: Vesicular stomatitis virus

<400> SEQUENCE: 1

Met Ala Ile Val Gly Ile Val Leu Leu Ile Val Val Thr Phe Leu Ala
1               5                   10                  15

Ile Lys Thr

<210> SEQ ID NO 2
<211> LENGTH: 21
<212> TYPE: PRT

<213> ORGANISM: Vesicular stomatitis virus

<400> SEQUENCE: 2

Phe Phe Phe Ile Ile Gly Leu Ile Ile Gly Leu Phe Leu Val Leu Arg
1               5                   10                  15

Val Gly Ile His Leu
            20

<210> SEQ ID NO 3
<211> LENGTH: 21
<212> TYPE: PRT
<213> ORGANISM: Vesicular stomatitis virus

<400> SEQUENCE: 3

Val Leu Ala Val Ile Ile Gly Phe Val Ile Leu Met Phe Leu Ile Lys
1               5                   10                  15

Leu Ile Gly Val Leu
            20

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Arg Ser Arg Lys Tyr Thr Ser Trp Tyr Val Ala Leu Lys Arg
1               5                   10

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Met Ala Lys Ser Ile Arg Ser Lys His Arg Arg Gln Met Arg Met Met
1               5                   10                  15

Lys Arg Glu

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Met Ala Arg Arg Arg Arg His Arg Gly Pro Arg Arg Pro Arg Pro Pro
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Synthetic peptide

<400> SEQUENCE: 7

Gly Arg Cys Arg Arg Leu Ala Asn Phe Gly Pro Arg Lys Arg Arg Arg
1               5                   10                  15

Arg Arg Arg

```
<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Arg Lys Arg Asn Arg Asp Ala Arg Arg Arg Arg Arg Lys Gln
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic peptide

<400> SEQUENCE: 9

Met Gln Arg Lys Pro Thr Ile Arg Arg Lys Asn Leu Arg Leu Arg Arg
1               5                   10                  15

Lys

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ile Met Arg Arg Arg Gly Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Lys Lys Leu Lys Lys Arg Asn Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Arg Arg Arg Ala Asn Asn Arg Arg Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Arg Lys Lys Arg Lys Lys Lys
```

```
1               5
```

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

```
Lys Arg Lys Gly Lys Leu Lys Asn Lys Gly Ser Lys Arg Lys Lys
1               5                   10                  15
```

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide

<400> SEQUENCE: 15

```
Ser Lys Arg Leu Ser Ser Arg Ala Arg Lys Arg Ala Ala Lys Arg Arg
1               5                   10                  15

Leu Gly
```

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide

<400> SEQUENCE: 16

```
Lys Arg Pro Arg Arg Arg Pro Ser Arg Pro Phe Arg Lys Pro
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

```
Lys Lys Arg Thr Leu Arg Lys Asn Asp Arg Lys Lys Arg
1               5                   10
```

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

```
Trp Arg Arg Gln Ala Arg Phe Lys
1               5
```

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Arg Lys Lys Arg Arg Gln Arg Arg
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Tyr Ala Arg Ala Ala Ala Arg Gln Ala Arg Ala
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide

<400> SEQUENCE: 21

Lys Gly Arg Gln Val Lys Val Trp Phe Gln Asn Arg Arg Met Lys Trp
1               5                   10                  15

Lys Lys

<210> SEQ ID NO 22
<211> LENGTH: 32
<212> TYPE: PRT
<213> ORGANISM: Artificial Sequence
<220> FEATURE:
<223> OTHER INFORMATION: Synthetic peptide

<400> SEQUENCE: 22

Met Ala Ile Val Gly Ile Val Leu Leu Ile Val Val Thr Phe Leu Ala
1               5                   10                  15

Ile Lys Thr Lys Lys Arg Thr Leu Arg Lys Asn Asp Arg Lys Lys Arg
            20                  25                  30

<210> SEQ ID NO 23
<211> LENGTH: 34
<212> TYPE: PRT
<213> ORGANISM: Artificial Sequence
<220> FEATURE:
<223> OTHER INFORMATION: Synthetic peptide

<400> SEQUENCE: 23

Phe Phe Phe Ile Ile Gly Leu Ile Ile Gly Leu Phe Leu Val Leu Arg
1               5                   10                  15

Val Gly Ile His Leu Lys Lys Arg Thr Leu Arg Lys Asn Asp Arg Lys
            20                  25                  30

Lys Arg

<210> SEQ ID NO 24
<211> LENGTH: 34
<212> TYPE: PRT
<213> ORGANISM: Artificial Sequence
<220> FEATURE:
<223> OTHER INFORMATION: Synthetic peptide

```
<400> SEQUENCE: 24

Val Leu Ala Val Ile Ile Gly Phe Val Ile Leu Met Phe Leu Ile Lys
1               5                   10                  15

Leu Ile Gly Val Leu Lys Lys Arg Thr Leu Arg Lys Asn Asp Arg Lys
            20                  25                  30

Lys Arg
```